(12) United States Patent
Sato

(10) Patent No.: US 11,647,974 B2
(45) Date of Patent: May 16, 2023

(54) X-RAY DIAGNOSTIC APPARATUS AND X-RAY DIAGNOSTIC METHOD

(71) Applicant: CANON MEDICAL SYSTEMS CORPORATION, Otawara (JP)

(72) Inventor: Daisuke Sato, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 14 days.

(21) Appl. No.: 17/319,688

(22) Filed: May 13, 2021

(65) Prior Publication Data
US 2021/0353240 A1 Nov. 18, 2021

(30) Foreign Application Priority Data

May 15, 2020 (JP) .............................. JP2020-086252
May 10, 2021 (JP) .............................. JP2021-079542

(51) Int. Cl.
*A61B 6/00* (2006.01)
*A61B 6/10* (2006.01)

(52) U.S. Cl.
CPC ............ *A61B 6/4429* (2013.01); *A61B 6/107* (2013.01); *A61B 6/5205* (2013.01); *A61B 6/542* (2013.01)

(58) Field of Classification Search
CPC ....... A61B 6/107; A61B 6/4429; A61B 6/488; A61B 6/5205; A61B 6/542; A61B 6/587; A61B 6/588; A61B 6/4458; A61B 6/4464; A61B 6/4452; A61B 6/06; A61B 6/4028; A61B 6/486; A61B 6/487
See application file for complete search history.

(56) References Cited

U.S. PATENT DOCUMENTS

| 9,788,810 | B2 * | 10/2017 | Ancar | A61B 6/547 |
| 2003/0007594 | A1 * | 1/2003 | Ganin | A61B 6/488 378/22 |
| 2008/0152088 | A1 * | 6/2008 | Wang | H04N 5/32 378/98.12 |
| 2009/0016484 | A1 * | 1/2009 | Wang | A61B 6/544 378/19 |
| 2011/0038454 | A1 * | 2/2011 | Minnigh | A61B 6/587 378/62 |
| 2012/0051498 | A1 * | 3/2012 | Koishi | A61B 6/5205 378/10 |
| 2012/0155609 | A1 * | 6/2012 | Lemminger | A61B 6/4283 378/98.2 |

(Continued)

FOREIGN PATENT DOCUMENTS

JP 2014-033953 A 2/2014

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

According to one embodiment, an X-ray diagnostic apparatus includes processing circuitry. The processing circuitry is configured to control an X-ray tube to perform an X-ray irradiation, that is performed prior to an X-ray imaging performed on an object, based on an imaging condition where at least one of an X-ray irradiation range and dose is smaller than an imaging condition of the X-ray imaging. Further, the processing circuitry is configured to evaluate a positional relationship between the X-ray tube and an X-ray detector based on a detection result of an X-ray irradiated in the prior X-ray irradiation by the X-ray detector.

9 Claims, 11 Drawing Sheets

(56) References Cited

U.S. PATENT DOCUMENTS

| | | | |
|---|---|---|---|
| 2012/0201354 A1* | 8/2012 | Kimura | A61B 6/505 378/62 |
| 2013/0077749 A1* | 3/2013 | Akahori | A61B 6/584 378/62 |
| 2015/0049862 A1* | 2/2015 | Ancar | A61B 6/588 378/190 |
| 2015/0055753 A1* | 2/2015 | Tajima | A61B 6/4283 378/62 |
| 2015/0110245 A1* | 4/2015 | Kim | A61B 6/488 378/62 |
| 2016/0051209 A1* | 2/2016 | Suzuki | A61B 6/5205 378/62 |
| 2016/0106382 A1* | 4/2016 | Lu | A61B 6/06 600/428 |
| 2016/0106387 A1* | 4/2016 | Kahn | A61B 6/4028 378/62 |
| 2017/0055936 A1* | 3/2017 | Okuno | A61B 6/4452 |
| 2017/0112460 A1* | 4/2017 | Merckx | A61B 6/542 |
| 2017/0265826 A1* | 9/2017 | Ancar | G03B 42/02 |
| 2018/0153488 A1* | 6/2018 | Ancar | A61B 6/465 |
| 2019/0046130 A1* | 2/2019 | Imamura | A61B 6/465 |
| 2019/0113652 A1* | 4/2019 | Allen | A61B 6/50 |
| 2019/0282194 A1* | 9/2019 | Tkaczyk | A61B 6/4405 |
| 2019/0380668 A1* | 12/2019 | Richard | A61B 6/08 |
| 2020/0069260 A1* | 3/2020 | Okuno | A61B 6/46 |
| 2020/0085385 A1* | 3/2020 | Nye | A61B 6/032 |
| 2021/0186452 A1* | 6/2021 | Imai | A61B 6/542 |

* cited by examiner

X-RAY DIAGNOSTIC APPARATUS AND X-RAY DIAGNOSTIC METHOD

CROSS-REFERENCE TO RELATED APPLICATIONS

This application claims the benefit of priority of Japanese Patent Application No. 2020-086252, filed May 15, 2020, the entire contents of which are incorporated herein by reference. Further, the contents of Japanese Patent Application No. 2021-079542, filed May 10, 2021, which claims priority to Japanese Patent Application No. 2020-086252, are also incorporated herein by reference in their entirety.

FIELD

Embodiments described herein relate generally to an X-ray diagnostic apparatus and an X-ray diagnostic method.

BACKGROUND

Some X-ray diagnostic apparatuses have a configuration in which the X-ray tube and the X-ray detector are not mechanically opposite to each other, and their positional relationship is not fixed. In this type of X-ray diagnostic apparatus, the positions of the X-ray tube and the X-ray detector can be set independently and freely.

When using this type of X-ray diagnostic apparatus, it is important to minimize the misalignment between the X-ray irradiation range of the X-ray tube and the detection range (X-ray receiving area) of the X-ray detector in order to ensure that the X-rays emitted from the X-ray tube are detected by the X-ray detector to generate an image. However, it is difficult to visually check whether the X-ray tube and the X-ray detector are in a predetermined positional relationship. A position detection device including an optical camera may be used to detect the positions of the X-ray tube and X-ray detector, but in this case, an additional configuration is required. In addition, when the inspection is performed in a limited space, such as in an X-ray device installed in the visiting car for rounds, the position detection device may not function properly because of obstacles such as peripheral equipment.

DETAILED DESCRIPTION

Hereinbelow, a description will be given of an X-ray diagnostic apparatus and an X-ray diagnostic method according to embodiments of the present invention with reference to the drawings.

In general, according to one embodiment, an X-ray diagnostic apparatus includes processing circuitry. The processing circuitry is configured to control an X-ray tube to perform an X-ray irradiation, that is performed prior to an X-ray imaging performed on an object, based on an imaging condition where at least one of an X-ray irradiation range and dose is smaller than an imaging condition of the X-ray imaging. Further, the processing circuitry is configured to evaluate a positional relationship between the X-ray tube and an X-ray detector based on a detection result of an X-ray irradiated in the prior X-ray irradiation by the X-ray detector.

An X-ray diagnostic apparatus according to an embodiment may be an X-ray tube and an X-ray detector configured to be movable independently of each other for X-ray imaging. The X-ray diagnostic apparatus includes general radiography devices, X-ray devices installed on the visiting car for rounds, X-ray angiography devices, X-ray TV devices, and the like.

Figure 1:
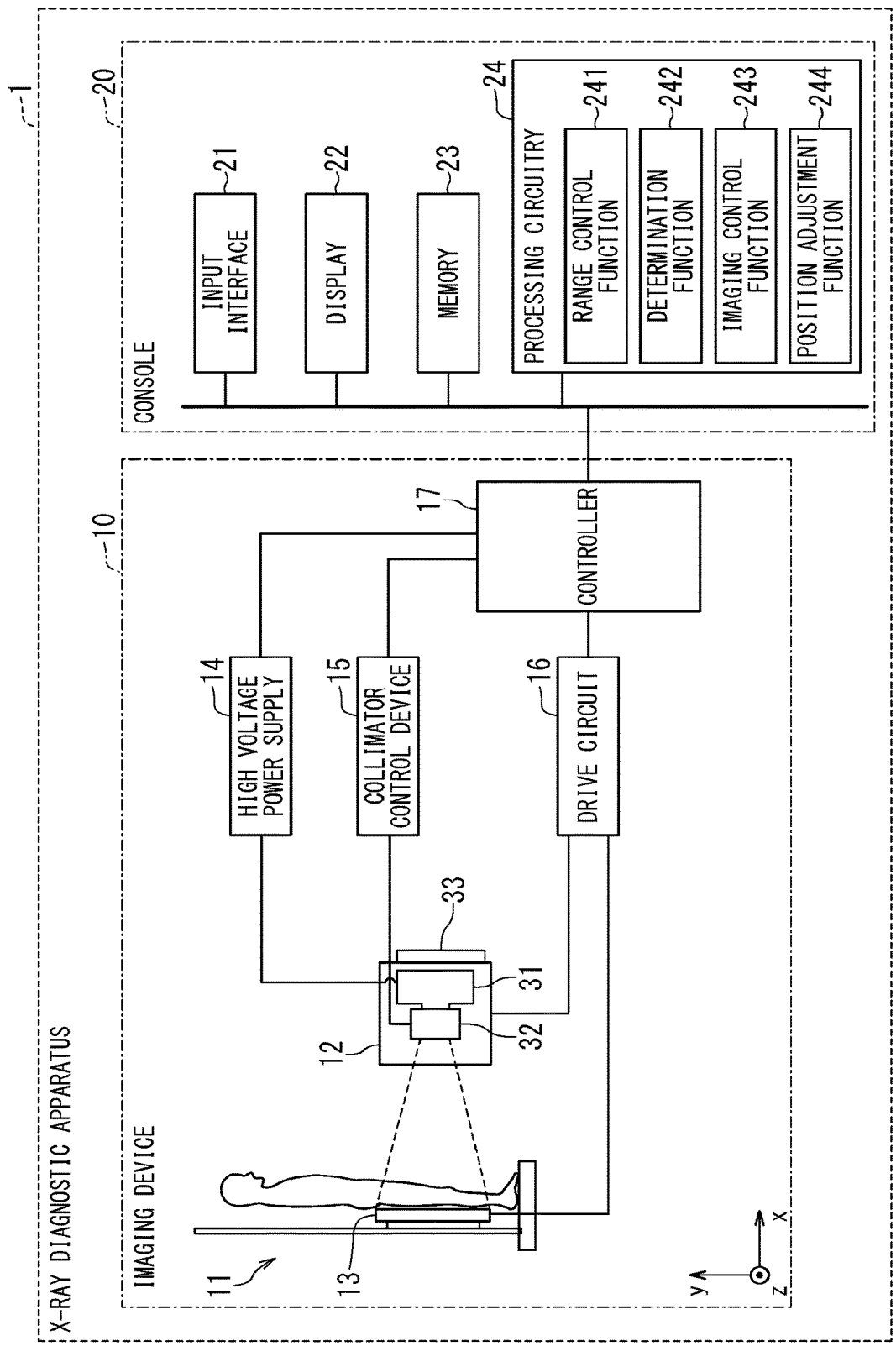
FIG. 1 is a block diagram showing an example of an X-ray diagnostic apparatus according to an embodiment of the present invention.
Figure 2:
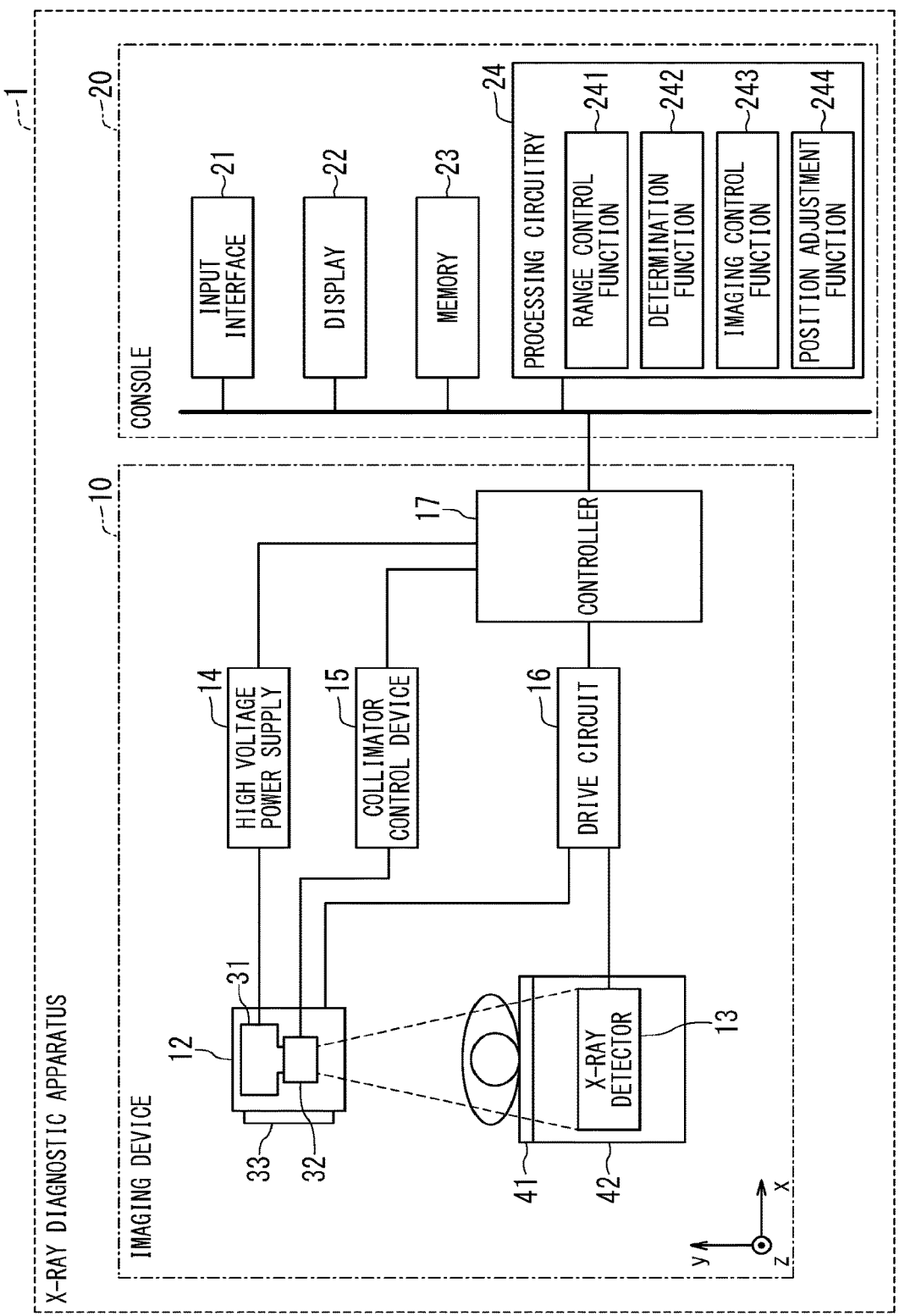
FIG. 2 is a block diagram showing another example of the X-ray diagnostic apparatus.

FIG. 1 is a block diagram showing an example of an X-ray diagnostic apparatus 1 according to an embodiment. FIG. 2 is a block diagram showing another example of the X-ray diagnostic apparatus 1. FIG. 1 is an example of the X-ray diagnostic apparatus 1 for performing X-ray imaging of an object in a standing position, and FIG. 2 is an example of X-ray diagnostic apparatus 1 for performing X-ray imaging of the object in a decubitus position.

The X-ray diagnostic apparatus 1 includes an imaging device 10 and a console 20 as shown in FIGS. 1 and 2. When performing X-ray imaging of the object in a standing position, the imaging device 10 includes a stand 11, an X-ray tube holding device 12, an X-ray detector 13 movably supported with respect to the stand 11, a high voltage power supply 14, a collimator control device 15, a drive circuit 16, and a controller 17. When performing X-ray imaging of the object in a decubitus position, as shown in FIG. 2, the imaging device 10 has a bed 42 provided with a top plate 41 on which the object is placed instead of the stand 11.

The X-ray tube holding device 12 of the imaging device 10 has an X-ray tube 31, a collimator 32, and an operation panel 33.

When performing X-ray imaging of the object in the standing position, as shown in FIG. 1, the object stands in front of the stand 11. At least one of the X-ray tube holding device 12 and the X-ray detector 13 is controlled by the processing circuitry 24 of the console 20 via the drive circuit 16 to move to change the positional relationship between the X-ray tube 31 and the X-ray detector 13. The movement of the X-ray tube holding device 12 and the X-ray detector 13 includes parallel translation along the X-ray irradiation axis, parallel translation in the direction orthogonal to the X-ray irradiation axis, and rotations.

When performing X-ray imaging of the object in the decubitus position, the object in the decubitus position is placed on the top plate 41 as shown in FIG. 2. In this case, as in the case of the standing position, at least one of the X-ray tube holding device 12 and the X-ray detector 13 is controlled by the processing circuitry 24 of the console 20 via the drive circuit 16 to move to change the positional relationship between the X-ray tube 31 and the X-ray detector 13.

The X-ray detector 13 is constituted by a flat panel detector (FPD) having a plurality of X-ray detection elements arranged in a two-dimensional array to detect an X-ray irradiated to the X-ray detector 13 through the object. The X-ray detector 13 outputs, based on the detected X-ray image, image data such as fluoroscopic data generated by X-ray fluoroscopy (hereinafter referred to as fluoroscopy), which captures time-sequential X-ray images (frame images) in real time, and plain radiography data generated by plain radiography, which captures plain radiographic image, to the console 20. The X-ray detector 13 may include an image intensifier, a TV camera, and the like, or may be a CMOS-FPD with a plurality of X-ray detectors each composed of semiconductor elements accumulating electric charges according to the amount of X-ray incident.

The X-ray tube 31 is a vacuum tube which irradiates thermoelectrons from the cathode (filament) to the anode (target) by applying a high voltage from the high voltage power supply 14.

The high voltage power supply 14 is composed of an electric circuit such as a transformer and a rectifier, and includes a high voltage generator having a function of generating a high voltage to be applied to the X-ray tube 31 and an X-ray control device that controls the output voltage according to the X-ray emitted by X-ray tube 31.

The collimator 32 includes a plurality of lead plates or the like for adjusting the X-ray irradiation range generated by the X-ray tube 31, and forms a slit by combining the plurality of lead plates or the like. For example, the collimator 32 has a plurality of pairs of movable blades, which are controlled by the processing circuitry 24 via the collimator control device 15 to adjust the irradiation range of X-rays irradiated from the X-ray tube 31 by opening and closing each pair of movable blades.

The operation panel 33 is provided on the body of the X-ray tube holding device 12 and has a hard key, such as a button for outputting a unique instruction signal to the processor when pressed by the user, and a display input device. The display input device includes a display as a display unit and a touch sensor as an input unit provided in the vicinity of the display.

The display of the operation panel 33 displays various images such as an image showing information regarding the X-ray diagnostic apparatus 1. The user can input various instructions for the image displayed on the display to the X-ray diagnostic apparatus 1 via the touch sensor or hard key of the operation panel 33. The operation panel 33 provides the processing circuitry 24 of the console 20 with a signal according to the user input. The X-ray diagnostic apparatus 1 may not include the operation panel 33.

The controller 17 has at least a processor and a memory, and is controlled by the processing circuitry 24 of the console 20 to generally control components of the imaging device 10.

Meanwhile, the console 20 has an input interface 21, a display 22, a memory 23, and a processing circuitry 24. The console 20 may not be provided independently. For example, the operation panel 33 of the imaging device 10 may have the functions of the input interface 21 and the display 22 of the console 20, and the processor and the memory of the controller 17 may have the functions of the processing circuitry 24 and the memory 23, respectively. The following description assumes that all functions are performed by a single console, but these functions may be performed by multiple consoles.

The input interface 21 of the console 20 includes, for example, a general pointing device such as a joystick, a trackball, a trackball mouse, a keyboard, a touch panel, a ten key, a hand switch for instructing X-ray emission timing, and provides operation signals corresponding to the user operation to the processing circuitry 24.

The display 22 is configured by a general display output device such as a liquid crystal display or an OLED (Organic Light Emitting Diode) display, and displays information in accordance with the control of the processing circuitry 24.

The memory 23 has a configuration including a processor readable recording medium such as a magnetic or optical recording medium or a semiconductor memory, and some or all of the programs and data in the storage medium may be configured to be downloaded via an electronic network.

The processing circuitry 24 is a processor that reads out and executes programs stored in the memory 23 to execute a process for easily obtaining the positional relationship between the X-ray tube 31 and the X-ray detector 13 without using any position detection device. Further, the processing circuitry 24 generally controls components of the imaging device 10 via the controller 17.

The processing circuitry 24 is configured to be able to determine whether the X-ray tube 31 and the X-ray detector 13 have a predetermined positional relationship.

Here, "the X-ray tube 31 and the X-ray detector 13 are in a predetermined positional relationship (hereinafter referred to as the predetermined positional relationship)" means that, for example, when fluoroscopy is performed by the X-ray diagnostic apparatus 1, the X-ray tube 31 and the X-ray detector 13 are in a positional relationship that satisfies the same regulation as those applied to fluoroscopic devices such as X-ray angiography devices. The positional relationship that satisfies this regulation includes the positional relationship in which the amount of protrusion of the X-ray irradiation area from the edge of the X-ray receiving area (image receiving surface) 131 during fluoroscopy or plain radiography is kept within a predetermined value. The regulation requires that X-ray irradiation in fluoroscopy and plain radiography be prohibited when the amount of protrusion of the X-ray irradiation range from the edge of the X-ray receiving area 131 of the X-ray detector 13 is larger than the predetermined value.

When the X-ray diagnostic apparatus 1 has an auto-positioning function, the predetermined positional relationship is the positional relationship between the X-ray tube 31 and the X-ray detector 13 in which X-rays are actually irradiated to the estimated irradiation range corresponding to the imaging conditions obtained by the auto positioning function. The auto positioning function automatically moves the X-ray tube 31 and X-ray detector 13 to the imaging position corresponding to the inspection, and may be performed by the processing circuitry 24 based on the information of the target imaging region included in the inspection information.

In addition, when pre-imaging is performed to confirm the positional relationship between the X-ray tube 31 and the X-ray detector 13 and to align them if necessary before plain radiography by the X-ray diagnostic apparatus 1, the predetermined positional relationship is the positional relationship between the X-ray tube 31 and the X-ray detector 13 in which X-rays are actually irradiated to the estimated irradiation range on the X-ray receiving area 131 that is estimated from the intended focus-to-image receiving surface distance (hereinafter referred to as SID) in plain radiography and the aperture of the collimator 32.

In order to determine whether or not the X-ray tube 31 and the X-ray detector 13 are in the predetermined positional relationship, the processing circuitry 24 controls the X-ray tube 31 to perform X-ray irradiation prior to an X-ray imaging such as fluoroscopy and plain radiography based on imaging conditions in which at least one of the X-ray irradiation range and dose is smaller than that of the X-ray imaging to be performed on the object.

It should be noted that the "X-ray irradiation to be performed prior to the X-ray imaging" is different from X-ray irradiation for X-ray imaging such as fluoroscopy and plain radiography, and may include pre-photography for setting imaging conditions for plain radiography.

By setting the X-ray irradiation range of the X-ray irradiation performed prior to the X-ray imaging (hereinafter referred to as initial irradiation) smaller than the X-ray irradiation range of the subsequent X-ray imaging, the exposure dose to the object in the initial irradiation can be reduced compared with that in the subsequent X-ray imaging, even if the X-ray conditions for the initial irradiation and the subsequent X-ray imaging are the same. Similarly, when the dose of initial irradiation is set smaller than that of the subsequent X-ray imaging, the exposure dose to the object can be reduced in the initial irradiation compared with that in the subsequent X-ray imaging, even if the X-ray irradiation ranges of the initial irradiation and the subsequent X-ray imaging are the same. Therefore, it is possible to determine whether the X-ray tube 31 and the X-ray detector 13 are in a predetermined positional relationship with a smaller exposure dose than the subsequent X-ray irradiation by performing the initial irradiation based on imaging conditions in which at least one of the X-ray irradiation range and dose is smaller than that of the subsequent X-ray imaging.

The following description shows an example of a case in which the X-ray tube 31 is controlled to irradiate X-rays prior to the X-ray imaging such as fluoroscopy and plain radiography at an initial irradiation range 51 smaller than an X-ray irradiation range (hereinafter referred to as second irradiation range) in the subsequent X-ray imaging.

In this case, the processor of the processing circuitry 24 realizes the range control function 241, the determination function 242, the imaging control function 243, and the position adjustment function 244, as shown in FIGS. 1 and 2. Each of these functions is stored in memory 23 in the form of a program. Some of the functions 241-244 of the processing circuitry 24 may be realized by an external processor connected to the imaging device 10 so as to be able to transmit/receive data, or by the processor of the controller 17.

Next, the configuration and operation of the functions 241-244 of the processing circuitry 24 in this case will be described.

Figure 3:
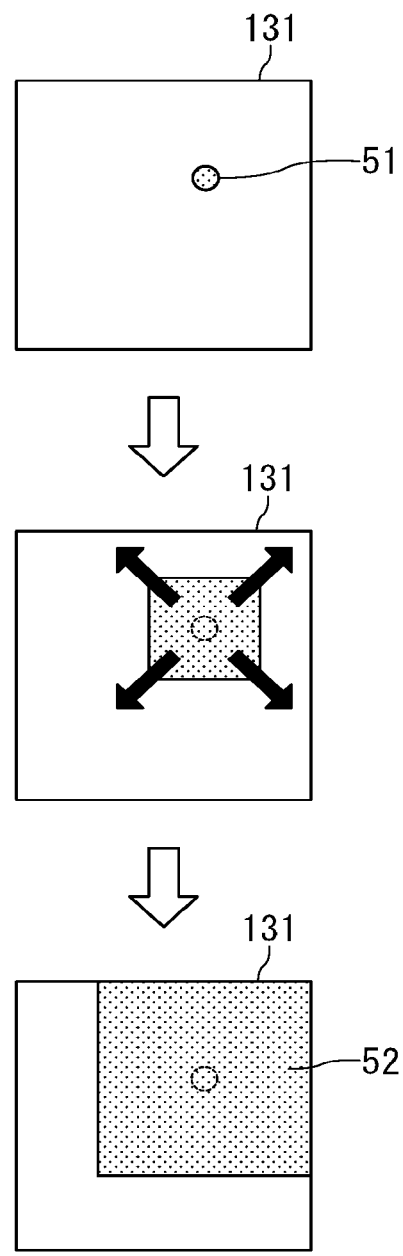
FIG. 3 is an explanatory diagram showing an example of a method of determining the positional relationship between an X-ray tube and an X-ray detector when the initial irradiation range is a range corresponding to a pencil beam.

FIG. 3 is an explanatory diagram showing an example of a method of determining the positional relationship between the X-ray tube 31 and the X-ray detector 13 when the initial irradiation range 51 is a range corresponding to a pencil beam.

The range control function 241 controls the X-ray tube 31 such that, prior to the X-ray imaging such as fluoroscopy and plain radiography performed on an object, X-ray irradiation is performed based on imaging conditions in which at least one of the X-ray irradiation range and dose is smaller than the X-ray imaging.

As mentioned above, the following description shows an example of a case in which the X-ray tube 31 is controlled to irradiate X-rays, prior to the X-ray imaging such as fluoroscopy and plain radiography, at the initial irradiation range 51 that is smaller than the X-ray irradiation range (second irradiation range) in the X-ray imaging.

When irradiating X-rays at the initial irradiation range 51, the positional relationship between the X-ray tube 31 and the X-ray detector 13 is unknown. Hence, it is preferable for the imaging control function 243 to prohibit fluoroscopy or plain radiography at this stage.

The upper part of FIG. 3 shows an example where the initial irradiation range 51 is the range corresponding to the so-called pencil beam. For example, when a fine pencil beam is slightly irradiated from the center of the X-ray shielding range even when the aperture blades of the collimator 32 are in fully closed state, the initial irradiation range 51 can be made small as shown in the upper part of FIG. 3 by simply fully closing the aperture blades.

The smaller the initial irradiation range 51 is, the easier it is to identify the center position of the X-ray irradiation range and the lower the exposure dose to the object and the user. When irradiating X-rays in the initial irradiation range 51, the X-ray condition including tube voltage and tube current is preferably set to the conditions that reduce the exposure compared to the X-ray conditions when performing normal fluoroscopy or plain radiography in the subsequent X-ray imaging, and is preferably to be the minimum conditions that can be set in the X-ray diagnostic apparatus 1. The shape of the initial irradiation range 51 may be a polygon such as a rectangular, or a circle or an oval.

The determination function 242 evaluates the positional relationship between the X-ray tube 31 and the X-ray detector 13 by, for example, determining whether the X-ray tube 31 and the X-ray detector 13 are in the predetermined positional relationship, based on the detection results of X-rays irradiated in the initial irradiation range 51 (see the upper row of FIG. 3) detected by the X-ray detector 13.

When the initial irradiation range 51 is small, such as the range corresponding to a pencil beam as shown in FIG. 3, and when the determination function 242 determines that the X-ray tube 31 and the X-ray detector 13 are in the predetermined positional relationship, the range control function 241 controls the X-ray tube 31 and the collimator 32 in front of the X-ray tube 31 to expand the X-ray irradiation range such that X-rays are irradiated in the second irradiation range 52 which is wider than the initial irradiation range 51 but within the X-ray receiving area 131 of the X-ray detector 13, as shown in the middle and bottom rows of FIG. 3. When the imaging region is predetermined, the size of the second irradiation range 52 may be set according to the imaging region under the condition that the range 52 is within the X-ray receiving area 131.

The range control function 241 evaluates the position of the initial irradiation range 51. When all X-rays irradiated in the initial irradiation range 51 fall on the X-ray detector 13, the center of the irradiation range can be determined. In this case, the range control function 241 can find the second irradiation range 52 that falls within the X-ray receiving area 131 based on the estimated center. Therefore, the second irradiation range 52 does not protrude from the X-ray receiving area 131 and satisfies the regulation for fluoroscopy.

The imaging control function 243 prohibits fluoroscopy or plain radiography when the X-ray tube 31 and the X-ray detector 13 are not in the predetermined positional relationship. In this case, fluoroscopy will be interlocked. Contrary, the imaging control function 243 permits fluoroscopy or plain radiography when the X-ray tube 31 and the X-ray detector 13 are in the predetermined positional relationship.

The following specific description with FIGS. 3-8 as references is an example in which the imaging control function 243 prohibits fluoroscopy as an example of X-ray imaging when X-rays are irradiated at the initial irradiation range 51.

As shown in the upper row of FIG. 3, when the initial irradiation range 51 is detected by the X-ray detector 13, the determination function 242 determines that the X-ray tube 31 and the X-ray detector 13 are in the predetermined positional relationship. Based on the result of this determination, the imaging control function 243 then permits fluoroscopy, which was prohibited during the initial irradiation of X-rays in the initial irradiation range 51. In this case, imaging device 10 can start fluoroscopy of the object, for example.

In the example shown in the upper row of FIG. 3, when the initial irradiation range 51 is not detected by the X-ray detector 13, the determination function 242 determines that the X-ray tube 31 and the X-ray detector 13 are not in the predetermined position relationship. Based on such determination, the imaging control function 243 prohibits fluoroscopy.

When information on fluoroscopy is needed emergently, it is preferable for the imaging control function 243 to permit fluoroscopy immediately after the determination function 242 determines that the X-ray tube 31 and the X-ray detector 13 are in the predetermined positional relationship while expanding the irradiation range. In this case, the imaging control function 243 may permit fluoroscopy when the irradiation range becomes larger than a predetermined irradiation range.

According to the imaging device 10, the positional relationship between the X-ray tube 31 and the X-ray detector 13 can be easily ascertained without using an additional configuration such as a position detection device, even when the X-ray diagnostic apparatus 1 is configured such that the X-ray tube 31 and the X-ray detector 13 can be moved independently of each other.

Fluoroscopy can be interlocked when the positional relationship does not meet the same regulations/standards as those applied to X-ray angiography devices and other fluoroscopic devices. Therefore, even when the X-ray diagnostic apparatus 1 is configured such that the X-ray tube 31 and the X-ray detector 13 can be moved independently of each other, fluoroscopy of the object can be safely performed in compliance with the regulation.

Figure 4A:
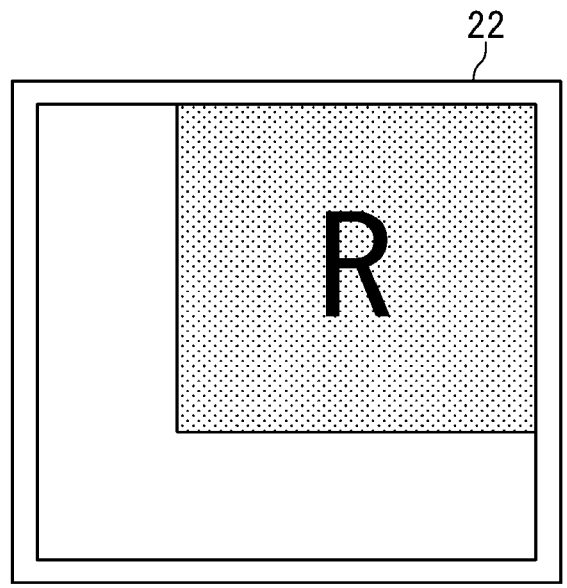
FIG. 4A is an explanatory diagram showing an example of an image displayed on a display after the start of fluoroscopy.
Figure 4B:
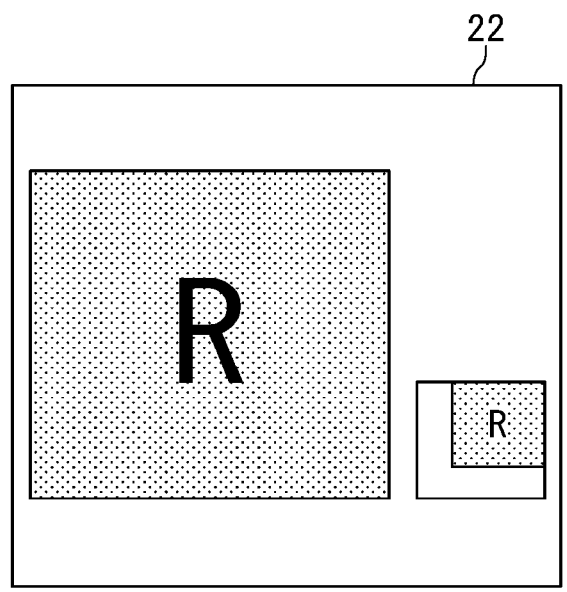
FIG. 4B is an explanatory drawing showing another example of an image displayed on the display after the start of fluoroscopy.

FIG. 4A is an explanatory diagram showing an example of an image displayed on the display 22 after the start of fluoroscopy, and FIG. 4B is an explanatory drawing showing another example of an image displayed on the display 22 after the start of fluoroscopy.

When fluoroscopy is started, an image showing the position of the irradiation range within the X-ray receiving area 131 may be displayed to adjust the position of the irradiation range (see FIG. 4A). In this case, the image showing only the irradiation range and the image showing the position of the irradiation range within the X-ray receiving area 131 may be generated and displayed in different windows but on the same display, or these images may be displayed on different displays, e.g., the display 22 and the display of the operation panel 33 (see FIG. 4B)

According to the imaging device 10, the user can easily adjust the position while checking the fluoroscopic image, thus unnecessary radiation exposure due to re-imaging caused by misalignment can be prevented.

Figure 5A:
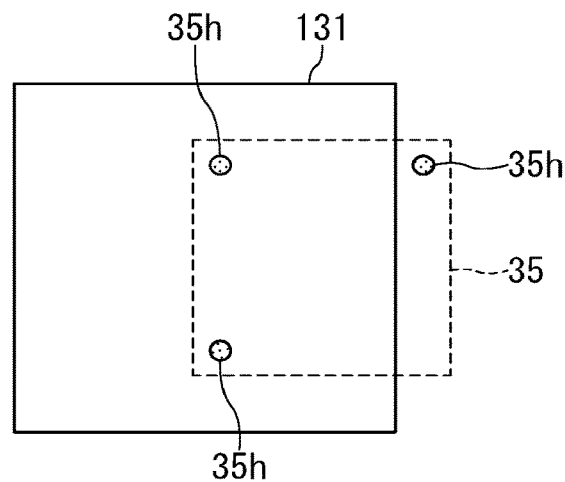
FIG. 5A is an explanatory diagram showing an example of a case where the X-ray tube and the X-ray detector are determined to be not in a predetermined positional relationship when the initial irradiation range corresponds to the imaging region of the object.
Figure 5B:
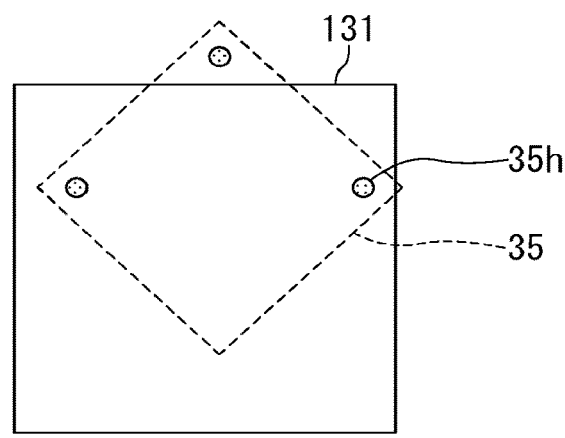
FIG. 5B is an explanatory diagram showing another example of a case where the X-ray tube and the X-ray detector are determined to be not in the predetermined positional relationship when the initial irradiation range corresponds to the imaging region of the object.
Figure 5C:
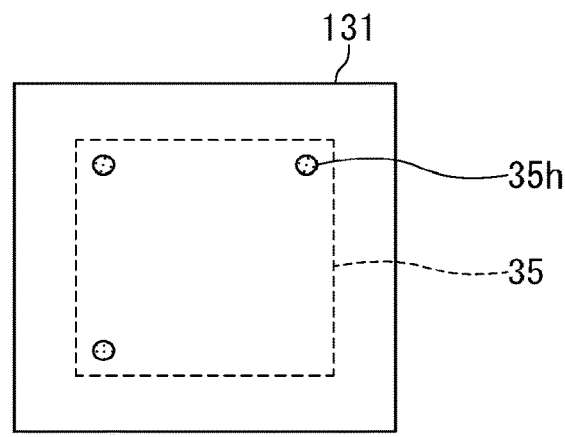
FIG. 5C is an explanatory diagram showing an example of a case where the X-ray tube and the X-ray detector are determined to be in the predetermined positional relationship when the initial irradiation range corresponds to the imaging region of the object.

FIG. 5A is an explanatory diagram showing an example of a case where the X-ray tube 31 and the X-ray detector 13 are determined to be not in the predetermined positional relationship when the initial irradiation range 51 corresponds to the imaging region of the object, and FIG. 5B illustrates another example. FIG. 5C is an explanatory diagram showing an example of a case where the X-ray tube and the X-ray detector are determined to be in the predetermined positional relationship when the initial irradiation range corresponds to the imaging region of the object.

In the example shown in FIG. 5, unlike the example shown in FIG. 3, the initial irradiation range 51 is set to the range corresponding to the imaging region, and the collimator 32 is controlled by the range control function 241 such that the aperture corresponds to the initial irradiation range 51.

In this example, the imaging device 10 is further provided with a shielding plate 35 that shields the initial irradiation range 51. The shielding plate 35 is composed of an X-ray shielding material such as lead, for example, and has at least three transmission portions 35h provided in the peripheral region thereof. The transmission portions 35h transmit X-rays. Each transmission portion 35h may be a hole in the shielding plate 35, or may be composed of an X-ray transmission material such as a filter. When the shielding plate 35 is rectangular, the transmission portions 35h may be located near three of the four vertices (see FIG. 5A).

The determination function 242 determines whether the X-ray tube 31 and the X-ray detector 13 are in the predetermined positional relationship based on the detection results of the X-rays transmitted through the transmission portions 35h by the X-ray detector 13. The determination function 242 may determine that the X-ray tube 31 and the X-ray detector 13 are not in the predetermined position when not all the transmission portions 35h are detected (see FIG. 5A and FIG. 5B), while the determination function 242 may determine that they are in the predetermined position when all transmission portions 35h are detected (see FIG. 5C).

When the imaging device 10 is provided with the shielding plate 35, at least three transmission areas corresponding to transmission portions 35h can be detected. In this case, when the shape of the figure formed by connecting the three transmission areas is different from the original shape of figure (e.g., a right-angled isosceles triangle), it is assumed that the X-ray tube 31 is tilted and is not directly opposite the X-ray detector 13 (i.e., the irradiation axis is not perpendicular to the X-ray detector 13 and the shielding plate 35 is not parallel to the X-ray detector 13). Therefore, when the shape of the figure formed by connecting the three transmission areas on the X-ray detector 13 is different from the original shape of figure, the determination function 242 may determine that the X-ray tube 31 and the X-ray detector 13 are not in the predetermined positional relationship even if all transmission portions 35h are detected.

When it is determined that they are in the predetermined positional relationship, the imaging control function 243 permits fluoroscopy. In this case, plain radiography and fluoroscopy of the imaging region can be performed as soon as the shielding plate 35 is removed. Hence, compared to the case where the positional relationship is determined using the pencil beam, the inspection can be started earlier because of the time required to expand the irradiation range.

The size of the irradiation range differs depending on the object and the region to be inspected. Thus, the shielding plate 35 can be preferred to be prepared in advance in several different size.

Next, the method of adjusting the position before fluoroscopy is permitted by the imaging control function 243 will be explained.

The position adjustment function 244 controls the drive circuit 16 that drives the x-ray tube 31 and the x-ray detector 13 based on the detection results of the X-rays irradiated in the initial irradiation range 51 by the X-ray detector 13 to automatically move at least one of the X-ray tube 31 and the X-ray detector 13 such that the x-ray tube 31 and the x-ray detector 13 are in the predetermined position relationship.

Figure 6:
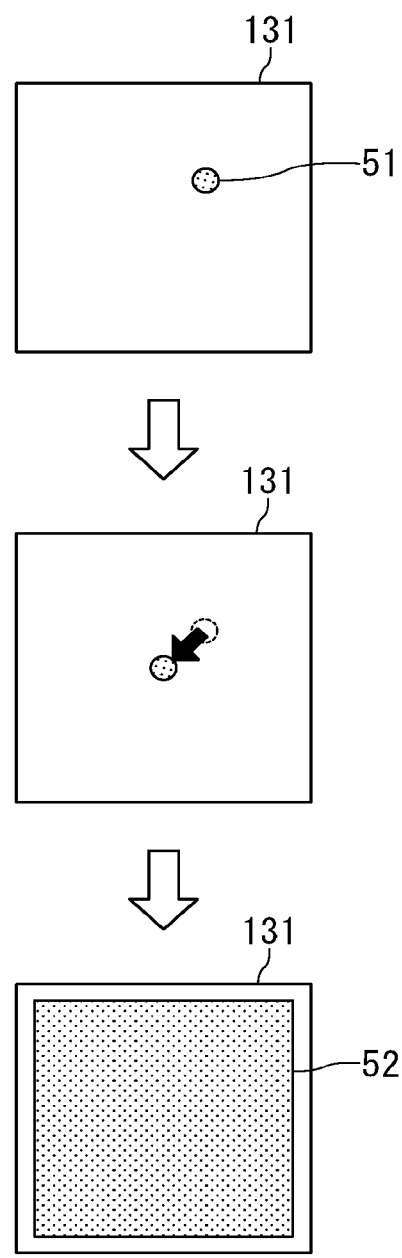
FIG. 6 is a diagram for explaining an example of a position adjustment method based on the center position of the initial irradiation range.

FIG. 6 is a diagram for explaining an example of a position adjustment method based on the center position of the initial irradiation range 51.

The center of the initial irradiation range 51 can be obtained as described above when the X-rays irradiated in the initial irradiation range 51 fall within the X-ray detector 13 as shown in the upper row of FIG. 3 and the upper row of FIG. 6. In this case, the position adjustment function 244 adjusts the positional relationship between the X-ray tube 31 and the X-ray detector 13 by moving at least one of the X-ray tube 31 and the X-ray detector 13 such that the center of the initial irradiation range 51 coincides with the center of the X-ray receiving area 131. (see the middle row of FIG. 6). The range control function 241 then expand the irradiation range by controlling the collimator 32 to irradiate X-rays at the second irradiation range 52 that is within the X-ray receiving area 131 of the X-ray detector 13 (see the middle row of FIG. 6). When the irradiation range is expanded after the center position is adjusted, the maximum size of the second irradiation range 52 can be increased compared to the case where the center position is not adjusted (see the bottom row of FIG. 3), and a wide field of view can be secured.

Figure 7:
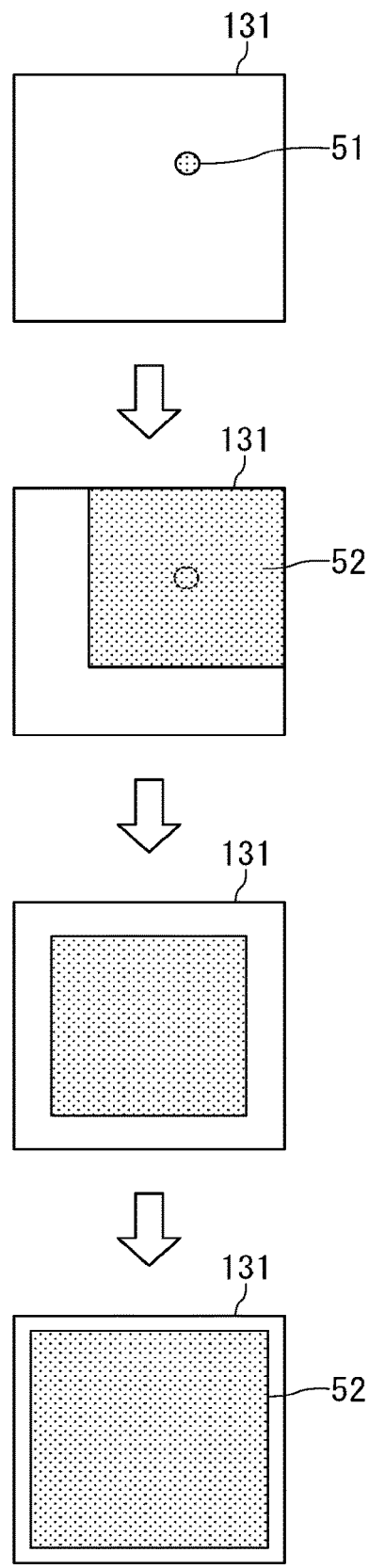
FIG. 7 is a diagram for explaining an example of a position adjustment method based on the second irradiation range.

FIG. 7 is a diagram for explaining an example of a position adjustment method based on the second irradiation range 52.

After expanding the irradiation range to the second irradiation range 52 without adjusting the center position as shown in the lower row of FIG. 3 (see the top row and the second row in FIG. 7), at least one of the X-ray tube 31 and the X-ray detector 13 may be moved (see the third row in FIG. 7) to further expand the second irradiation range 52 (see the bottom row in FIG. 7). Even in this case, the maximum size of the second irradiation range 52 can be increased compared to the case where no position adjustment is made (see the bottom row of FIG. 3), and a wide field of view can be secured.

Figure 8:
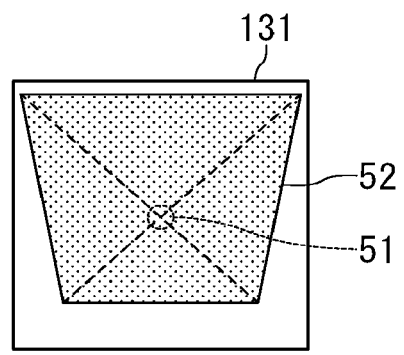
FIG. 8 is a diagram for explaining an example of a position adjustment method when an aperture shape of the collimator is rectangular and the X-ray tube and the X-ray detector are not directly opposite each other.
Figure 8:
Figure 8:
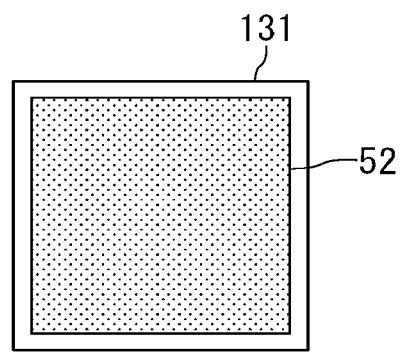

FIG. 8 is a diagram for explaining an example of a position adjustment method when an aperture shape of the collimator 32 is rectangular and the X-ray tube 31 and the X-ray detector 13 are not directly opposite each other.

In the state shown in the second or third row of FIG. 7, the irradiation range has already been expanded, and an area having a shape corresponding to the shape of the irradiation aperture of the collimator 32 has been projected onto the X-ray receiving area 131. In this case, the orientation of the irradiation aperture of the collimator 32 can be evaluated based on the shape of the detection range detected by the X-ray receiving area 131.

In this context, the determination function 242 determines whether the shape of the observed detection range where the X-ray detector 13 detected X-rays matches the shape of the estimated detection area of X-rays on the X-ray detector 13, which is estimated from the shape of the aperture of the collimator 32. When the determination function 242 determines that the shape of the observed detection range does not match the shape of the estimated detection range, the position adjustment function 244 adjusts the angle of at least one of the X-ray tube 31 and the X-ray detector 13 by controlling the drive circuit 16 such that the shape of the observed detection range approaches the shape of the estimated detection range.

For example, in a case where the shape of the irradiation aperture of the collimator 32 is a rectangle, when the shape of the detection range detected on the X-ray receiving area 131 is a trapezoid, the X-ray tube 31 and the X-ray detector 13 are not directly opposite each other (skewed, tilted) as shown in FIG. 8. In this case, the position adjustment function 244 adjusts the angle of at least one of the X-ray tube 31 and the X-ray detector 13 by controlling the drive circuit 16 such that the trapezoidal shape of the observed detection range where the X-ray is detected by the X-ray detector 13 approaches a rectangle.

Meanwhile, when the determination function 242 determines that the shape of the observed detection range matches the shape of the estimated detection range, the imaging control function 243 may allow X-ray imaging such as fluoroscopy and plain radiography.

Even when the X-ray tube 31 and the X-ray detector 13 are directly opposite each other and the shape of the observed detection range matches the shape of the estimated detection range, the SID (focus-to-image receiving surface distance) may be different from the desired distance. Therefore, the position adjustment function 244 may calculate the size of the estimated detection range of X-rays in the X-ray detector 13 based on the desired SID and the aperture size of the collimator 32. In this case, the position adjustment function 244 adjusts the SID by moving at least one of the X-ray tube 31 and the X-ray detector 13 along the X-ray irradiation axis direction such that the size of the observed detection range approaches the size of the estimated detection range.

The X-ray diagnostic apparatus 1 including the imaging device 10 performs initial X-ray irradiation at the initial irradiation range 51, for example, with the maximum focused irradiation range (pencil beam) and the lowest X-ray conditions prior to the X-ray imaging like fluoroscopy at the beginning of a fluoroscopic procedure. Accordingly, the X-ray diagnostic apparatus 1 can determine whether the X-ray tube 31 and the X-ray detector 13 are in the predetermined position (e.g., whether they are aligned or not) based on the output of the X-ray detector 13 without using additional sensors such as position detection devices. Further, when the X-ray tube 31 and the X-ray detector 13 are in the predetermined positional relationship, the X-ray diagnostic apparatus 1 can determine that fluoroscopy is allowable and start fluoroscopy and output fluoroscopic data, while interlocking fluoroscopy when the X-ray tube 31 and the X-ray detector 13 are not in the predetermined positional relationship.

When the center of the initial irradiation range 51 can be detected by X-ray irradiation in the initial irradiation range 51, the irradiation range can be expanded within the range that does not protrude from the edge of the X-ray receiving area 131 because the maximum irradiation range that can be expanded within the X-ray receiving area 131 can be obtained from the initial irradiation range 51.

Therefore, it is possible to safely perform fluoroscopy according to the regulations even when the X-ray tube 31 and the X-ray detector 13 are configured to be movable independently of each other, such as a general radiography device, an X-ray device installed in the visiting car for rounds, or an X-ray TV device. Further, the position of the X-ray tube 31 and the direction of the irradiation opening of the collimator 32 can be automatically adjusted based on the shape of the irradiation range of fluoroscopy and the opening degree (aperture size) of the collimator 32.

Accordingly, the information obtained by the X-ray irradiation in the initial irradiation range 51 can be used to obtain the positional relationship between the X-ray tube 31 and the X-ray detector 13 for performing fluoroscopy.

The X-ray irradiation in the initial irradiation range 51 can also be used as the pre-imaging for setting imaging conditions for plain radiography. In this case, the imaging control function 243 prohibits plain radiography when irradiating X-rays in the initial irradiation range 51.

Further, the method of obtaining the positional relationship between the X-ray tube 31 and the X-ray detector 13 described above can be applied even after the start of fluoroscopy.

Figure 9:
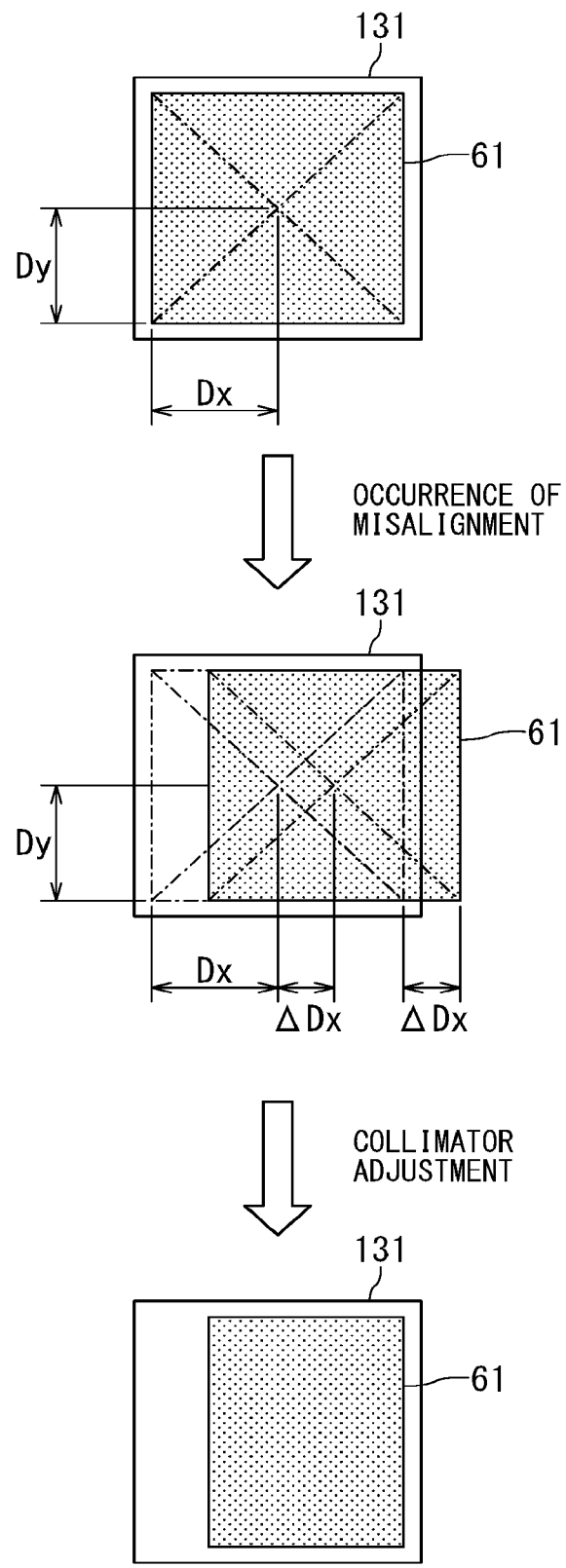
FIG. 9 is an explanatory diagram showing an example of a collimator control method when the relative positions of the X-ray tube and the X-ray detector change after the start of fluoroscopy.

FIG. 9 is an explanatory diagram showing an example of a collimator control method when the relative positions of the X-ray tube 31 and the X-ray detector 13 change after the start of fluoroscopy. It should be noted that the diagonal lines of the observed detection range 61 (the range where the X-ray detector 13 actually detected X-rays) shown in FIG. 9 are depicted only for convenience of explanation and are not detected by the X-ray detector 13.

After starting to perform the X-ray imaging such as fluoroscopy on an object, the determination function 242 evaluates in a time series manner whether the positional relationship between the X-ray tube 31 and the X-ray detector 13 satisfies the criteria. Specifically, the determination function 242 starts to obtain the observed detection range 61 (the range in which X-ray was actually detected by the X-ray detector 13) in a time series manner when fluoroscopy is started, and determines whether the amount of time variation in the relative position of the X-ray tube 31 and the X-ray detector 13 is equal to or greater than the threshold value based on the observed detection range 61. The amount of time variation may be determined by comparing the previous frame and the current frame at each frame or every few frames, or by averaging the results of multiple comparisons. The imaging control function 243 determines that when the amount of the time variation is equal to or greater than the threshold value, the relative position of the X-ray tube 31 and the X-ray detector 13 has momentarily been deviated significantly for some reason and that the collimator 32 is unable to handle the deviation. In this case, the imaging control function 243 controls the imaging device 10 to terminate fluoroscopy and prohibit subsequent fluoroscopy. Examples of such a case include a case where the X-ray diagnostic apparatus 1 does rounds in the hospital, after the X-ray detector 13 is inserted between the back of the object and the hospital bed, the X-ray detector 13 may move along with the object when the object turns over as instructed by the technician.

When a part of the observed detection range 61 moves outside the X-ray receiving area 131 of the X-ray detector 13 but the amount of time variation of the relative position of the X-ray tube 31 and the X-ray detector 13 is smaller than the threshold value (see the middle row of FIG. 9), the imaging control function 243 controls the collimator 32 to shield X-rays corresponding to the irradiation range outside the X-ray receiving area 131 of the X-ray detector 13 (see the lower row of FIG. 9).

Specifically, at the start of fluoroscopy, since all of the observed detection range 61 is within the X-ray receiving area 131, both the center coordinates and the size of the observed detection range 61 (e.g., width and height if it is a rectangle) can be obtained. Therefore, when the amount of time variation of the relative position of the X-ray tube 31 and the X-ray detector 13 is smaller than the threshold value, it is easy to control the aperture to narrow down the irradiation range based on the information on the center coordinates and the size of the observed detection range 61 such that irradiation range does not protrude outside the X-ray receiving area 131.

When X-rays are irradiated on the X-ray detector 13 at an angle, the shape of the observed detection range 61 becomes distorted, such as a trapezoidal shape when it should be a rectangle, or an oval shape when it should be a circle. In this case, when the shape of the observed detection range 61 is polygonal, for example, care should be taken to ensure that the longest side does not protrude from the X-ray receiving area 131.

Figure 10A:
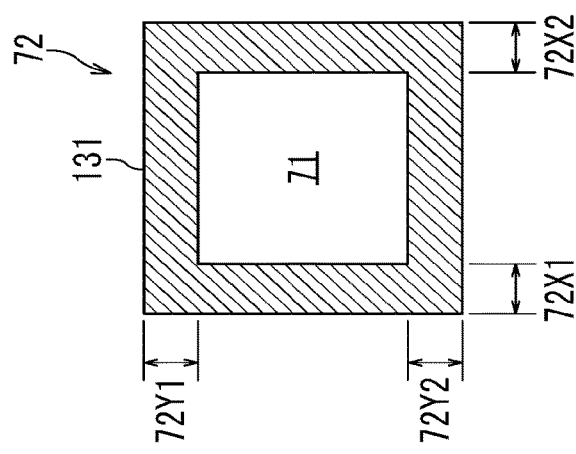
FIG. 10A is a diagram for explaining a misalignment detection area at the peripheral edge of the X-ray receiving area.
Figure 10B:
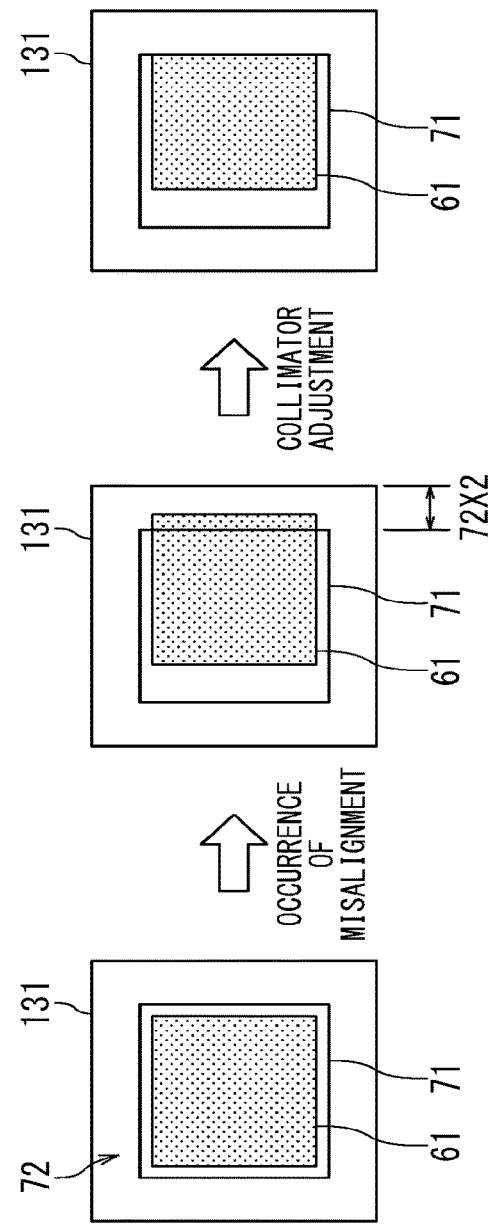
FIG. 10B is an explanatory diagram showing another example of a collimator control method when the relative positions of the X-ray tube and the X-ray detector change after the start of fluoroscopy.

FIG. 10A is a diagram for explaining a misalignment detection area 72 at the peripheral edge of the X-ray receiving area 131. FIG. 10B is an explanatory diagram showing another example of a collimator control method when the relative positions of the X-ray tube 31 and the X-ray detector 13 change after the start of fluoroscopy.

In the example shown in FIG. 10, the peripheral edge of the X-ray receiving area 131 is used as an area 72 for misalignment detection (hereinafter referred to as a misalignment detection area 72), and the protruded irradiation range from the detection area 71 surrounded by the misalignment detection area 72 is monitored. The data detected in the misalignment detection area 72 may be used only for misalignment (protrusion) detection, or may be used for both misalignment detection and imaging.

The misalignment detection area 72 includes areas 72X1 and 72X2, for example, having 10 columns of detection elements at both ends in the lateral direction of the X-ray receiving area 131, and areas 72Y1 and 72Y2 having 10 rows of detection elements at both ends in the horizontal direction of the X-ray receiving area 131 (see FIG. 10A).

When the misalignment detection area 72 is available, the determination function 242 can detect that the observed detection range 61 has entered the misalignment detection area 72 before the part of the observed detection range 61 is out of the X-ray receiving area 131. In this case, the imaging control function 243 may control the collimator 32 to shield the X-rays that have entered the misalignment detection area 72 (see FIG. 10B).

Further, in the cases shown in FIGS. 10A and 10B, like the case shown in FIG. 9, the determination function 242 determines whether the amount of time variation in the relative position of the X-ray tube 31 and the X-ray detector 13 is equal to or greater than the threshold value based on the observed detection range 61. Specifically, the determination function 242 may determine that the amount of time variation is equal to or greater than the threshold value when the observed detection range 61 intrudes into the misalignment detection area 72 more than the threshold intrusion width (e.g., 7 columns) with respect to the width of the misalignment detection area 72 (e.g., 10 columns in the area 72X2) in a predetermined frame period (e.g., one frame). In this case, as in the example shown in FIG. 9, the imaging control function 243 may determine that the collimator 32 is unable to handle the temporal deviation of the relative position of the X-ray tube 31 and the X-ray detector 13 when the amount of time variation is equal to or greater than the threshold value, and control the imaging device 10 to terminate fluoroscopy and prohibit subsequent fluoroscopy.

Figure 11:
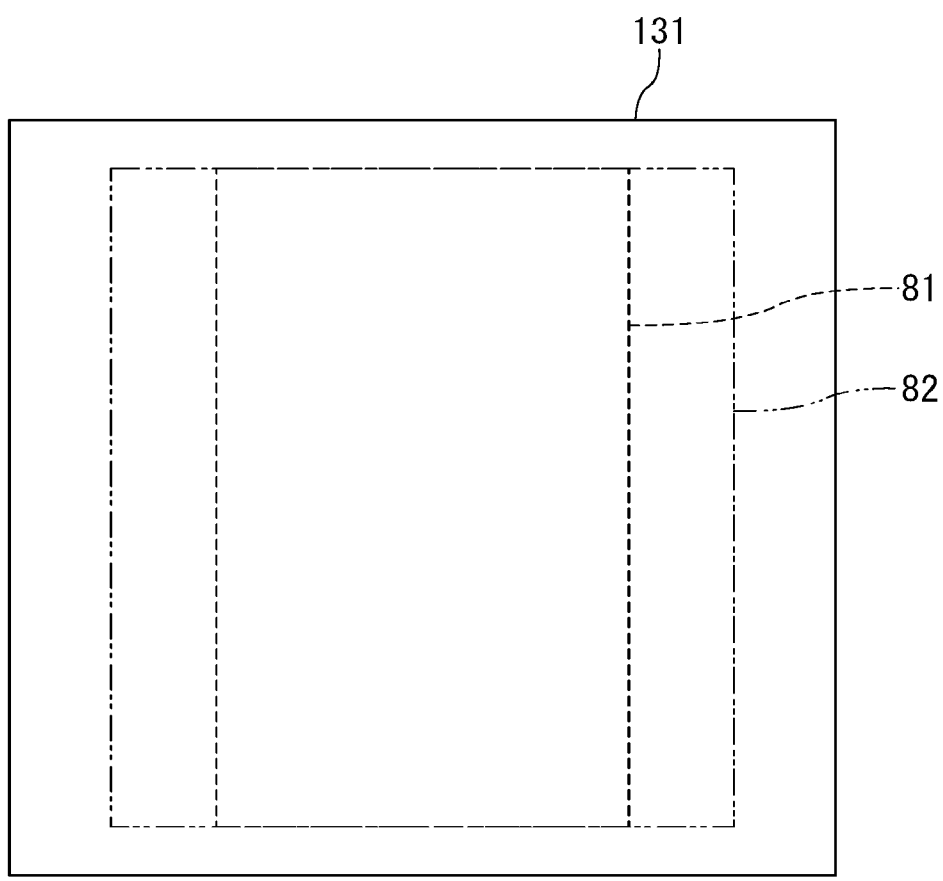
FIG. 11 is an explanatory diagram showing an example of a method of evaluating the accuracy of the auto-positioning function of the X-ray diagnostic apparatus.

FIG. 11 is an explanatory diagram showing an example of a method of evaluating the accuracy of the auto-positioning function of the X-ray diagnostic apparatus 1.

The method of obtaining the positional relationship between the X-ray tube 31 and the X-ray detector 13 described above can also be applied to the evaluation of the accuracy of the auto-positioning function of the X-ray diagnostic apparatus 1.

When the X-ray diagnostic apparatus 1 has the auto-positioning function, the positioning accuracy of the auto-positioning function may deteriorate over time, and the components may not be positioned accurately at the desired position. In this case, the internal parameters of the auto-positioning function can be corrected using the method of obtaining the positional relationship between the X-ray tube 31 and the X-ray detector 13 described above. For example, the accuracy of the auto-positioning function can be evaluated by comparing the observed detection range 61 with the correct range 81 in the X-ray receiving area 131, which is estimated to be the range in which X-rays will be detected if the function works correctly.

As shown in FIG. 11, the position of the threshold range 82 that encompasses the correct range 81 may be set in advance. In this case, when the observed detection range 61 protrudes from the threshold range 82, the processing circuitry 24 notifies the user of the information that an abnormality has occurred in the X-ray diagnostic apparatus 1 or that failure has occurred by displaying an image indicating such information on the display such as the display 22, or by outputting sound indicating the information through a speaker (not shown), or by making a serviceman call.

Accordingly, based on the fluoroscopic information, the X-ray diagnostic apparatus 1 can correct changes in the internal data of the X-ray diagnostic apparatus 1 over time and to detect malfunctions or failures, thereby maintaining the performance of the apparatus.

Further, automatic adjustment after executing auto-positioning function can be performed based on the fluoroscopic information. Therefore, the variation in the accuracy of position adjustment by the user can be reduced and the inspection throughput can be improved.

According to at least one of the above-described embodiments, the positional relationship between the x-ray tube 31 and the x-ray detector 13 can be easily obtained without using any position detection device.

The processing circuitry in the above-described embodiments is an example of the processing circuitry described in the claims. In addition, the term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors is provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray tube that performs an X-ray irradiation;
an X-ray detector that detects the X-ray irradiation as an X-ray detection result; and
processing circuitry configured to
control the X-ray tube to perform the X-ray irradiation, which is performed prior to an X-ray imaging performed on an object, based on a first imaging condition in which at least one of an X-ray irradiation range and a dose is smaller than a second imaging condition of the X-ray imaging;
acquire the X-ray detection result from the X-ray detector; and evaluate a positional relationship between the X-ray tube and the X-ray detector based on the X-ray detection result of the X-ray irradiated in the prior X-ray irradiation by the X-ray detector;

wherein the processing circuitry is further configured to
estimate a shape of the X-ray irradiation range based on a predetermined imaging condition;
determine whether a shape of the X-ray irradiation range in the X-ray detector matches the estimated shape of the X-ray irradiation range;
perform the X-ray imaging when it is determined that the shapes match, or prohibit the X-ray imaging when it is determined that the shapes do not match;
when it is determined that the shapes do not match, adjust the positional relationship between the X-ray tube and the X-ray detector such that the shape of the X-ray irradiation range in the X-ray detector becomes the shape of the estimated X-ray irradiation range; and
perform the X-ray imaging on the object based on the adjusted positional relationship.

2. The X-ray diagnostic apparatus according to claim 1, wherein the processing circuitry is further configured to:
determine whether the X-ray tube and the X-ray detector are directly opposite each other based on the X-ray detection result; and
permit the X-ray imaging when it is determined that the X-ray tube and the X-ray detector are directly opposite each other, or prohibit the X-ray imaging when it is determined that the X-ray tube and the X-ray detector are not directly opposite each other.

3. The X-ray diagnostic apparatus according to claim 1, wherein the processing circuitry is further configured to:
evaluate a position of the X-ray irradiation range irradiated by the X-ray irradiation in the X-ray detector based on the X-ray detection result;
expand the X-ray irradiation range such that the evaluated position of the X-ray irradiation range is centered on an expanded X-ray irradiation range and the expanded X-ray irradiation range is within a range according to an X-ray receiving area of the X-ray detector; and
perform the X-ray imaging on the object based on the expanded X-ray irradiation range.

4. The X-ray diagnostic apparatus according to claim 1, wherein the processing circuitry is further configured to:
estimate a size of the X-ray irradiation range based on the predetermined imaging conditions;
adjust a distance between the X-ray tube and the X-ray detector such that the shape of the X-ray irradiation range in the X-ray detector and a size of the X-ray irradiation range in the X-ray detector become the estimated shape and the size of the estimated X-ray irradiation range; and
perform the X-ray imaging on the object based on the adjusted distance.

5. The X-ray diagnostic apparatus according to claim 1, wherein the processing circuitry is further configured to:
adjust an angle between the X-ray tube and the X-ray detector such that the shape of the X-ray irradiation range in the X-ray detector is the estimated shape of the estimated X-ray irradiation range; and
perform the X-ray imaging on the object based on the adjusted angle.

6. The X-ray diagnostic apparatus according to claim 1, wherein the processing circuitry is further configured to:
start to perform the X-ray imaging on the object;
after starting to perform the X-ray imaging on the object, evaluate in a time series manner whether an amount of time variation in a relative position of the X-ray tube and the X-ray detector is equal to or greater than a threshold value based on the X-ray detection result; and
control whether to continue or stop the X-ray imaging based on the amount of time variation.

7. The X-ray diagnostic apparatus according to claim 1, further comprising a shielding plate having at least three X-ray transmission portions transmitting X-rays irradiated from the X-ray tube,
wherein the processing circuitry is further configured to evaluate the positional relationship between the X-ray tube and the X-ray detector based on positions of X-rays transmitted through the X-ray transmission portions detected by the X-ray detector.

8. The X-ray diagnostic apparatus according to claim 3, wherein the processing circuitry is further configured to:
adjust the positional relationship between the X-ray tube and the X-ray detector such that the position of the X-ray irradiation range in the X-ray detector is located at a center of the X-ray receiving area; and
perform the X-ray imaging on the object based on the adjusted positional relationship.

9. An X-ray diagnostic method, comprising:
controlling an X-ray tube to perform an X-ray irradiation, that is performed prior to an X-ray imaging performed on an object, based on a first imaging condition where at least one of an X-ray irradiation range and a dose is smaller than a second imaging condition of the X-ray imaging;
detecting the X-ray irradiation with an X-ray detector, wherein the detection of the X-ray irradiation is a detection result;
acquiring the detection result and
evaluating a positional relationship between the X-ray tube and the X-ray detector based on the detection result of an X-ray irradiated in the prior X-ray irradiation by the X-ray detector;
wherein the method further comprises
estimating a shape of the X-ray irradiation range based on a predetermined imaging condition;
determining whether a shape of the X-ray irradiation range in the X-ray detector matches the estimated shape of the X-ray irradiation range; and
performing the X-ray imaging when it is determined that the shapes match, or prohibit the X-ray imaging when it is determined that the shapes do not match;
when it is determined that the shapes do not match, adjusting the positional relationship between the X-ray tube and the X-ray detector such that the shape of the X-ray irradiation range in the X-ray detector becomes the shape of the estimated X-ray irradiation range; and
performing the X-ray imaging on the object based on the adjusted positional relationship.

* * * * *